(12) United States Patent
Takehara et al.

(10) Patent No.: US 8,778,268 B2
(45) Date of Patent: Jul. 15, 2014

(54) SPECIMEN ANALYZER, ABNORMALITY CONTROL METHOD OF THE SAME AND COMPUTER PROGRAM PRODUCT

(75) Inventors: Hisato Takehara, Kobe (JP); Yuji Wakamiya, Kobe (JP); Tomoyuki Nishida, Ashiya (JP)

(73) Assignee: Sysmex Corporation, Kobe (JP)

( * ) Notice: Subject to any disclaimer, the term of this patent is extended or adjusted under 35 U.S.C. 154(b) by 1054 days.

(21) Appl. No.: 12/288,555

(22) Filed: Oct. 21, 2008

(65) Prior Publication Data
US 2009/0215183 A1 Aug. 27, 2009

(30) Foreign Application Priority Data
Feb. 27, 2008 (JP) ................. 2008-045723

(51) Int. Cl.
*G01N 35/02* (2006.01)
*G06F 11/00* (2006.01)
*G01N 35/00* (2006.01)

(52) U.S. Cl.
CPC ...... *G01N 35/00623* (2013.01); *G01N 35/0098* (2013.01); *G01N 35/025* (2013.01)
USPC ................ 422/67; 436/47; 702/182; 702/185

(58) Field of Classification Search
None
See application file for complete search history.

(56) References Cited

U.S. PATENT DOCUMENTS

2007/0172390 A1 7/2007 Ootani et al.
2009/0292492 A1* 11/2009 Nishida et al. ............ 702/85

FOREIGN PATENT DOCUMENTS

JP 03-183955 8/1991

* cited by examiner

*Primary Examiner* — P. Kathryn Wright
(74) *Attorney, Agent, or Firm* — Brinks Gilson & Lione

(57) ABSTRACT

Specimen analyzer includes a first holding section for holding a container; a first mechanism section for executing a first operation for the container on the first holding section; a second holding section for holding the container; a first transfer mechanism section for transferring the container from the first holding section to the second one; a second mechanism section for executing a second operation for the container on the second one; an error detector for detecting error in the first mechanism section; and an error controller for controlling the operation of the first holding section, the first and second operation so that the first operation and the transfer operation of the first holding section would be stopped while the second operation would be continued in case of the error in the first mechanism section. An abnormality control method of the analyzer and computer program product are also disclosed.

5 Claims, 6 Drawing Sheets

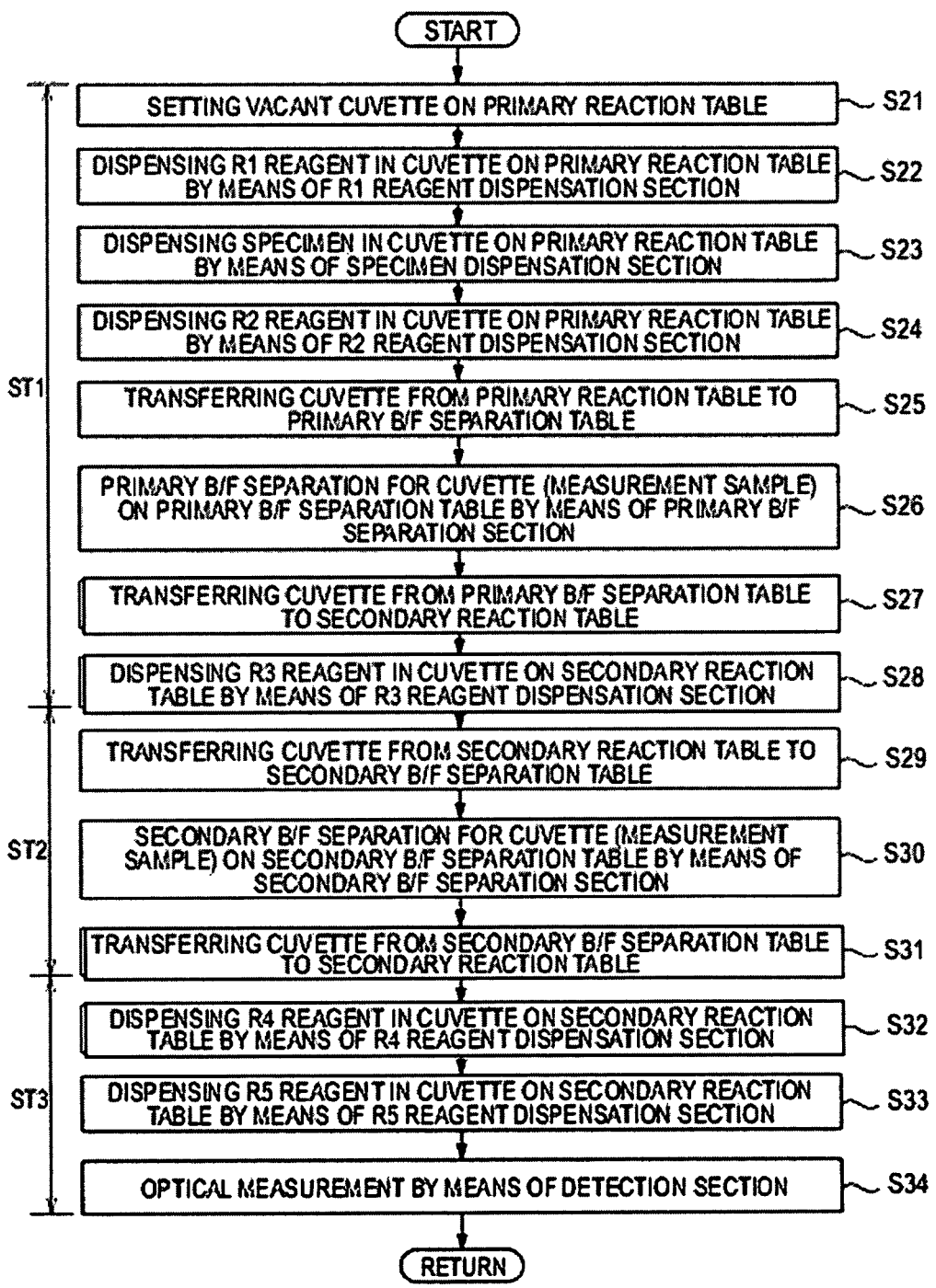

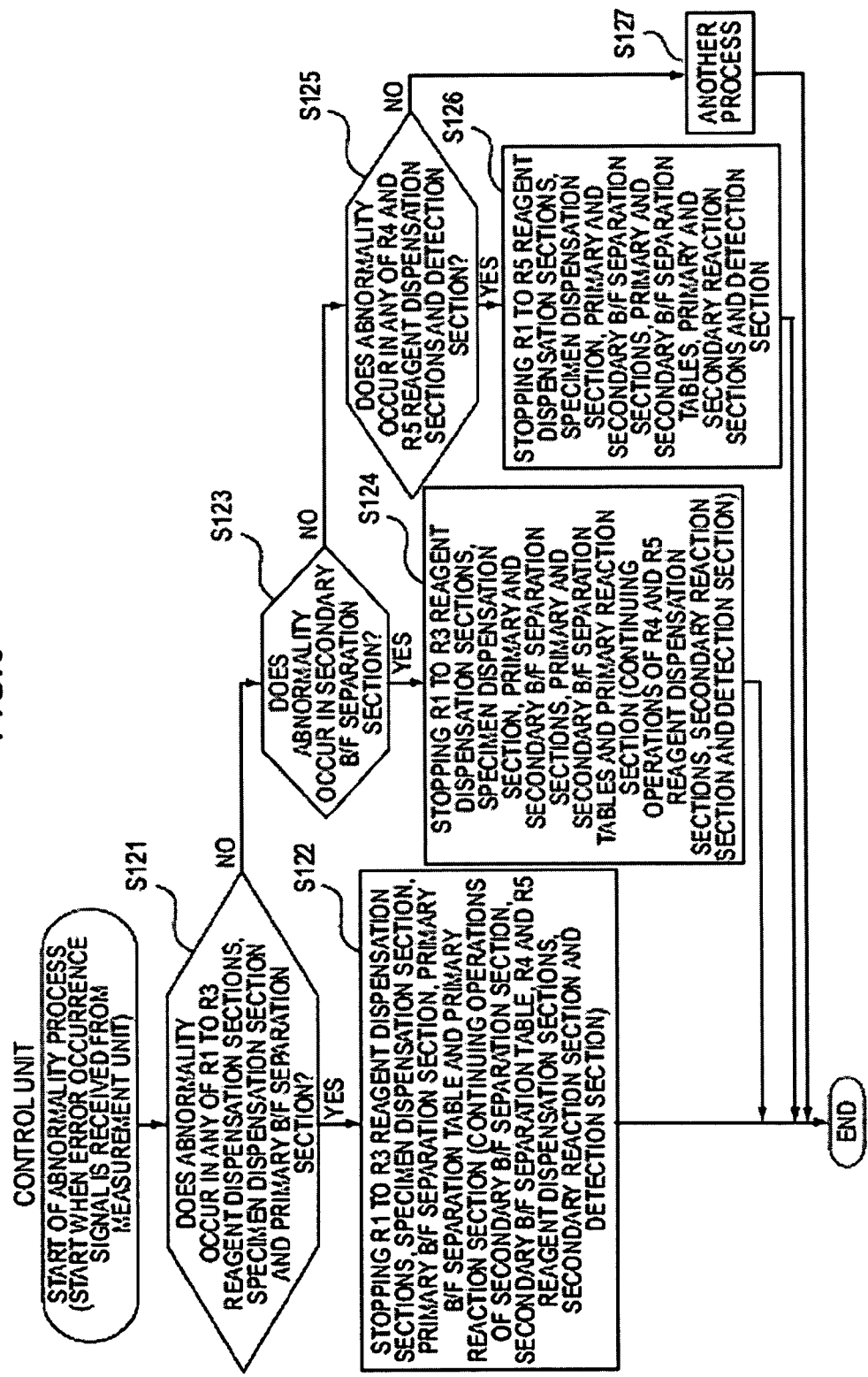

SPECIMEN ANALYZER, ABNORMALITY CONTROL METHOD OF THE SAME AND COMPUTER PROGRAM PRODUCT

RELATED APPLICATIONS

This application claims priority under 35 U.S.C. §119 to Japanese Patent Application No. JP2008-045723 filed on Feb. 27, 2008, the entire content of which is hereby incorporated by reference.

FIELD OF THE INVENTION

The present invention relates to a specimen analyzer for analyzing a specimen such as a device for immunoassay and a blood coagulation analyzing device, an abnormality control method of the same and a computer program product.

BACKGROUND

Improvement in processing performance of a specimen analyzer such as a device for immunoassay has been desired in order to process many specimens by means of plural kinds of reagent. Accordingly, the analyzer holds plural reaction containers for containing reagents and specimens and comprises a rotation table for moving the reaction containers smoothly to a predetermined position, plural dispensation sections for dispensing specimens or reagents into the reaction containers in accordance with an operation of the rotation table and the like.

In such an analyzer, an operation of the analyzer should be stopped when abnormality occurs during measurement of a specimen. Stopping all of the operations of the analyzer, however, causes suspension of measurement of a specimen having been mixed with a reagent. A specimen whose measurement has been suspended once cannot be used again. This causes a problem that the specimen and reagent are wasted.

For the purpose of solving the problem, disclosed in JP-A-H03-183955 is an automatic analyzing device in which a mechanism other than the section related to the reaction table and light measurement is stopped while operations of the reaction table and the light measurement are continued when abnormality related to any one of a specimen dispensation section, a reagent dispensation section and a stirring section occurs. Such a technology allows a part of the specimens to be continuously measured even in the case of occurrence of abnormality in any one of the specimen dispensation section, the reagent dispensation section and the stirring section, so that a waste of a specimen and a reagent may be reduced.

In the automatic analyzer in accordance with JP-A-H03-183955, an operation of the device is stopped in some cases under a condition that a pipette in the dispensation section is inserted in the reaction container held on the reaction table when abnormality occurs in the specimen dispensation section, the reagent dispensation section or the stirring section. In this case, abnormality occurring in a detection sensor for detecting a position of the pipette prevents the analyzer from detecting insertion of the pipette in the reaction container. This is likely to cause a pipette to be damaged when the reaction table operates or cause the reaction table not to be able to properly operate.

BRIEF SUMMARY

The scope of the present invention is defined solely by the appended claims, and is not affected to any degree by the statements within this summary.

A first aspect of the present invention is a specimen analyzer comprising: a first holding section for holding a container for containing at least one of a specimen, a reagent and a mixture thereof and transferring the container to a predetermined position; a first mechanism section for executing a predetermined first operation for the container held on the first holding section; a second holding section for holding the container; a first transfer mechanism section for transferring the container from the first holding section to the second holding section; a second mechanism section for executing a predetermined second operation for the container held on the second holding section; an error detector for detecting occurrence of abnormality in the first mechanism section; and an error controller for controlling operations of the first holding section and the first and second mechanism sections so that the first operation and the transfer operation of the first holding section would be stopped while the second operation would be continued in the case that the error detector detects occurrence of abnormality in the first mechanism section.

A second aspect of the present invention is a specimen analysis method comprising: (a) transferring a container containing at least one of a specimen, a reagent and a mixed liquid to a predetermined position by a first holding section for holding the container; (b) executing a predetermined first operation for the container held on the first holding section by means of a first mechanism section arranged to be able to access the container held on the first holding section; (c) transferring the container from the first holding section to the second holding section; (d) executing a predetermined second operation for the container held on the second holding section by means of the second mechanism section; and (e) stopping the transfer operation of the first holding section and the first operation and continuing the second operation in the case that occurrence of abnormality in the first mechanism section is detected.

A third aspect of the present invention is a computer program product, comprising: a computer readable medium; and instructions, on the computer readable medium, adapted to enable a general purpose computer to perform operations, comprising: (a) transferring a container containing at least one of a specimen, a reagent and a mixed liquid to a predetermined position by a first holding section for holding the container; (b) executing a predetermined first operation for the container held on the first holding section by means of a first mechanism section arranged to be able to access the container held on the first holding section; (c) transferring the container from the first holding section to the second holding section; (d) executing a predetermined second operation for the container held on the second holding section by means of the second mechanism section; and (e) stopping the transfer operation of the first holding section and the first operation and continuing the second operation in the case that occurrence of abnormality in the first mechanism section is detected.

BRIEF DESCRIPTION OF THE DRAWINGS

FIG. 5 is a flowchart showing a measurement process of the device for immunoassay shown in FIG. 1.

FIG. 6 is a flowchart showing an abnormality control process of a control unit of the device for immunoassay shown in FIG. 1.

DETAILED DESCRIPTION OF THE PREFERRED EMBODIMENTS

The preferred embodiments of the present invention will be described hereinafter with reference to the drawings.

Now, described in detail will be an embodiment of a specimen analyzer in accordance with the invention, made reference to the attached drawings.

[Whole Structure of the Device]

Figure 1:
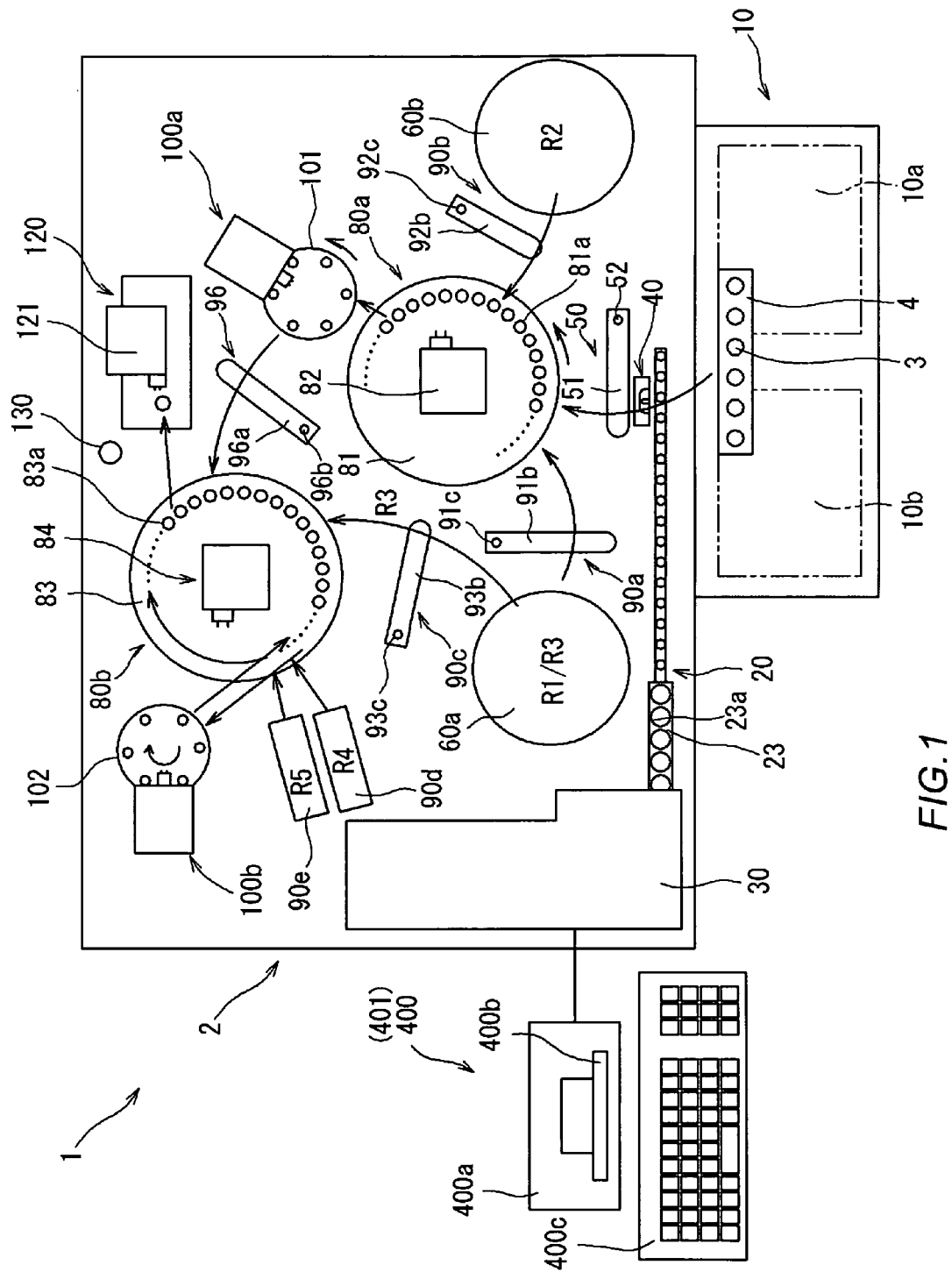
FIG. 1 is a flat illustration showing a whole structure of a device for immunoassay (a specimen analyzer) in accordance with an embodiment of the invention.
Figure 2:
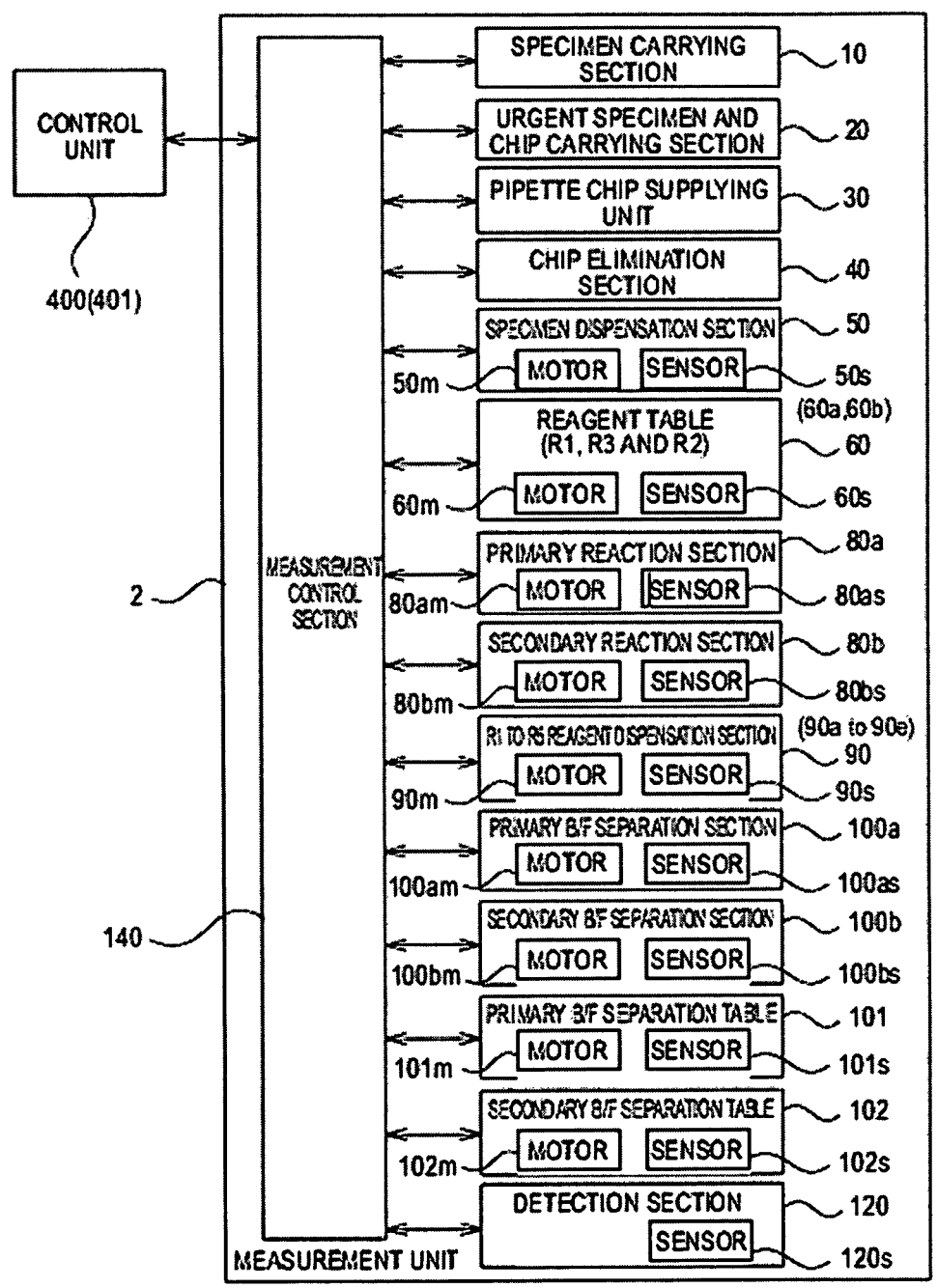
FIG. 2 is a block diagram showing a structure of a measurement unit of the device for immunoassay shown in FIG. 1.

FIG. 1 is a flat illustration showing a whole structure of a device for immunoassay (a specimen analyzer) in accordance with an embodiment of the invention. FIG. 2 is a block diagram showing a structure of a measurement unit in the device for immunoassay shown in FIG. 1.

An analyzer for immunoassay 1 in accordance with an embodiment of the invention is a instrument for using a specimen (a sample) such as blood to carry out inspection for various measurement items (analysis items) such as hepatitis B, hepatitis C, a tumor marker and thyroid hormone. As simply shown in FIG. 1, the analyzer for immunoassay 1 mainly comprises a measurement unit (a measurement section) 2 formed from plural mechanisms (components) and a control unit 400 electrically connected to the measurement unit 2, the control unit 400 being a data processing unit.

The measurement unit 2 comprises a specimen carrying section (a sampler) 10, an urgent specimen and chip carrying section 20, a pipette chip supplying unit 30, a chip elimination section 40, a specimen dispensation section 50, a reagent table 60 (60a and 60b), a primary reaction section 80a and a secondary reaction section 80b, a reagent dispensation section 90 (90a to 90e), a primary B/F separation section 100a and a secondary B/F separation section 100b, a primary B/F separation table 101 and a secondary B/F separation table 102, a detection section 120, a measurement control section 140 (refer to FIG. 2) for carrying out operation control of a mechanism such as the specimen carrying section (the sampler) 10 and the specimen dispensation section 50. In the analyzer for immunoassay 1 in accordance with the embodiment, a through-away pipette chip is changed every time suction and discharge of a specimen is carried out in order to prevent a specimen such as blood sucked and discharged by means of the specimen dispensation section 50 from being mixed with another specimen.

In the device for immunoassay 1, an antigen included in a specimen such as blood, which is subject to measurement, is combined with a capture antibody (a reagent R1) to form an antigen—capture antibody complex. The antigen—capture antibody complex is then combined with a magnetic particle (a reagent R2) to form an antigen—capture antibody complex—magnetic particle complex. Following to the above, the antigen—capture antibody—magnetic particle complex is attracted to a magnet of the primary BF (bound free) separation section 100a to eliminate an unreacted (free) capture antibody. The antigen—capture antibody—magnetic particle complex is then combined with a labeled antibody (reagent R3) to form a labeled antibody—antigen—capture antibody—magnetic particle complex. After the above, the labeled antibody—antigen—capture antibody—magnetic particle complex is attracted to a magnet of the secondary BF separation section 100b to eliminate an unreacted (free) labeled antibody. Further, added is a luminescent substrate (reagent R5) emitting light in a reaction process with the labeled antibody. Following to the above, measured is the amount of light emission generated from the reaction between the labeled antibody and the luminescent substrate. An antigen included in a specimen to be combined with the labeled antibody is quantitatively measured through such a process.

[Structure of Measurement Unit]

To a structure of each mechanism of the measurement unit 2, properly applied can be a well-known structure. The structure will be simply described hereinafter, made reference to FIGS. 1 to 3.

The specimen carrying section 10 is arranged to carry a rack 4 where plural test tubes 3 containing specimens are placed to a position corresponding to a sucking position of the specimen dispensation section 50, as shown in FIGS. 1 and 2. The specimen carrying section 10 includes a rack setting section 10a for setting the rack 4 where the test tube 3 containing unprocessed specimens is placed and a rack storage section 10b for storing the rack 4 where the test tube 3 containing specimens having undergone a dispensation process is placed. Carrying the test tube 3 containing unprocessed specimens to the position corresponding to the sucking position of the specimen dispensation section 50 allows the specimen dispensation section 50 to perform suction of the specimens such as blood in the test tube 3, and then, the rack 4 where the test tube 3 is placed to be stored in the rack storage section 10b.

The urgent specimen and chip carrying section 20 is arranged to carry the test tube 3, which contains an urgent specimen required to cut into the specimens carried by means of the specimen carrying section 10 for the purpose of inspection, to a position where the specimen dispensation section 50 is mounted.

The pipette chip supplying unit 30 has a function of placing provided pipette chips one by one in a chip setting section 23a of a carrying rack 23 of the urgent specimen and chip carrying section 20.

The chip elimination section 40 is provided for the purpose of eliminating the pipette chip mounted to the specimen dispensation section 50 described later.

The specimen dispensation section 50 has a function of dispensing the specimen in the test tube 3 carried to the sucking position by means of the specimen carrying section 10 in a cuvette (not shown) held on a holding section 81a of the primary reaction table 81 of the later-mentioned primary reaction section 80a. The specimen dispensation section 50 is arranged to be able to rotate an arm section 51 about a shaft 52 and move the arm section 51 in the vertical direction. At a top end part of the arm section 51, provided is a nozzle section for sucking and discharging a specimen. A pipette chip carried by means of a carrying rack (not shown) of the urgent specimen and chip carrying section 20 is mounted at a top end of the nozzle section.

The reagent table 60a is a rotation table driven to rotate. On the reagent table 60a, a reagent container for containing the reagent R1 including a capture antibody and a reagent container for containing the reagent R3 including a labeled antibody are set.

On the other hand, the reagent table 60b is a rotation table driven to rotate. On the reagent table 60b, a reagent container for containing the reagent R2 including a magnetic particle is set.

The primary reaction section 80a is provided for the purpose of rotating a cuvette held on the holding section 81a of the primary reaction table 81, which is driven to rotate, by a predetermined angle for every predetermined period (20 seconds in the embodiment) to transport the cuvette and for the purpose of stirring the specimen, the reagents R1 and R2 in the cuvette. That is to say, the primary reaction section 80a is provided in order to react the reagent R2 including a magnetic particle with an antigen in the specimen in the cuvette. The primary reaction section 80a is formed from the primary reaction table 81 for carrying a cuvette for containing a specimen and the reagents R1 and R2 in a rotation direction and a container carrying section 82 for stirring a specimen and the reagents R1 and R2 in a cuvette and carrying the cuvette containing the specimen and reagents R1 and R2, which have been stirred, to the later-mentioned primary B/F separation table 101.

The container carrying section 82 is rotatably set at a center part of the primary reaction table 81. The container carrying section 82 has a function of holding a cuvette held on the holding section 81a of the primary reaction table 81 and stirring a sample in the cuvette. Further, the container carrying section 82 also has a function of carrying a cuvette containing a sample incubated by stirring a specimen and the reagents R1 and R2 to the primary B/F separation table 101.

The reagent dispensation section 90a has a function of sucking the reagent R1 in a reagent container set on the reagent table 60a and dispensing the sucked reagent R1 in a cuvette of the primary reaction section 80a. The reagent dispensation section 90a is arranged so that an arm section 91b can be rotated about a shaft 91c and moved in the vertical direction. At a top end part of the arm section 91b, a nozzle section (a pipette) for sucking and discharging the reagent R1 in the reagent container is provided.

The reagent dispensation section 90b has a function of dispensing the reagent R2 in a reagent container set on the reagent table 60b in a cuvette of the primary reaction section 80a in which a specimen and the reagent R1 is dispensed. The reagent dispensation section 90b is arranged so that an arm section 92b can be rotated about a shaft 92c and moved in the vertical direction. At a top end part of the arm section 92b, a nozzle section (a pipette) for sucking and discharging the reagent R2 in the reagent container is provided.

The primary B/F separation section 100a is provided for separating the unreacted reagent R1 (an unnecessary component) and a magnetic particle from a sample in a cuvette carried by means of the container carrying section 82 of the primary reaction section 80a.

The cuvette of the primary B/F separation table 101 in which the unreacted reagent R1 and such has been dispensed is carried to a holding part 83a of the secondary reaction table 83 of the secondary reaction section 80b by means of a carrying mechanism 96.

The carrying mechanism 96 is arranged to be able to rotate an arm section 96a about a shaft 96b, the arm section 96a having a cuvette holding section (not shown) on its top end, and move the arm section 96a in the vertical direction.

The secondary reaction section 80b has a structure similar to that of the first reaction section 80a. The secondary reaction section 80b is provided for the purpose of rotating a cuvette held on the holding section 83a of the secondary reaction table 83 by a predetermined angle for every predetermined period (20 seconds in the embodiment) to transport the cuvette and for the purpose of stirring the specimen and the reagents R1, R2, R3, R4 and R5 in the cuvette. That is to say, the secondary reaction section 80b is provided in order to react the reagent R3 including a labeled antibody with an antigen in the specimen in the cuvette and in order to react the reagent R5 including a luminescent substrate with a labeled antibody of the reagent R3. The secondary reaction section 80b is formed from the secondary reaction table 83 for carrying a cuvette 8 for containing a specimen and the reagents R1, R2, R3, R4 and R5 in a rotation direction and a container carrying section 84 for stirring a specimen and the reagents R1, R2, R3, R4 and R5 in a cuvette and carrying the cuvette containing the specimen and such, which have been stirred, to the later-mentioned secondary B/F separation table 102. Further, the container carrying section 84 has a function of carrying a cuvette having been processed by means of the secondary B/F separation part 100b to the holding section 83a of the secondary reaction table 83 again.

The reagent dispensation section 90c has a function of sucking the reagent R3 in a reagent container set on the reagent table 60a and dispensing the sucked reagent R3 in a cuvette of the secondary reaction section 80b, the cuvette in which a specimen and the reagents R1 and R2 have been dispensed. The reagent dispensation section 90c is arranged so that an arm section 93b can be rotated about a shaft 93c and moved in the vertical direction. At a top end part of the arm section 93b, a nozzle section (a pipette) for sucking and discharging the reagent R3 in the reagent container is provided.

The secondary B/F separation section 100b has a structure similar to that of the primary B/F separation section 100a. The secondary B/F separation section 100b is provided for separating the unreacted reagent R3 (an unnecessary component) and a magnetic particle from a sample in a cuvette carried by means of the container carrying section 84 of the secondary reaction section 80b. The secondary B/F separation section 100b has no access to the primary reaction table 81.

The R4 reagent dispensation section 90d and the R5 reagent dispensation section 90e are provided for the purpose of moving nozzle sections, which are not shown, in the vertical direction to supply the cuvettes of the secondary reaction section 80b with the reagents R4 and R5, respectively. The R4 reagent dispensation section 90d and the R5 reagent dispensation section 90e have no access to the primary reaction table 81 and the secondary B/F separation table 102.

The detection section 120 is provided for the purpose of measuring the amount of an antigen included in a specimen having undergone a predetermined process by obtaining the amount of light emission generated in a reaction process between a labeled antibody combined with an antigen of the specimen and the luminescent substrate through a photo multiplier tube. The detection section 120 comprises a carrying mechanism section 121 for carrying a cuvette held on the holding section 83a of the secondary reaction table 83 of the secondary reaction section 80b to the detection section 120.

Figure 3:
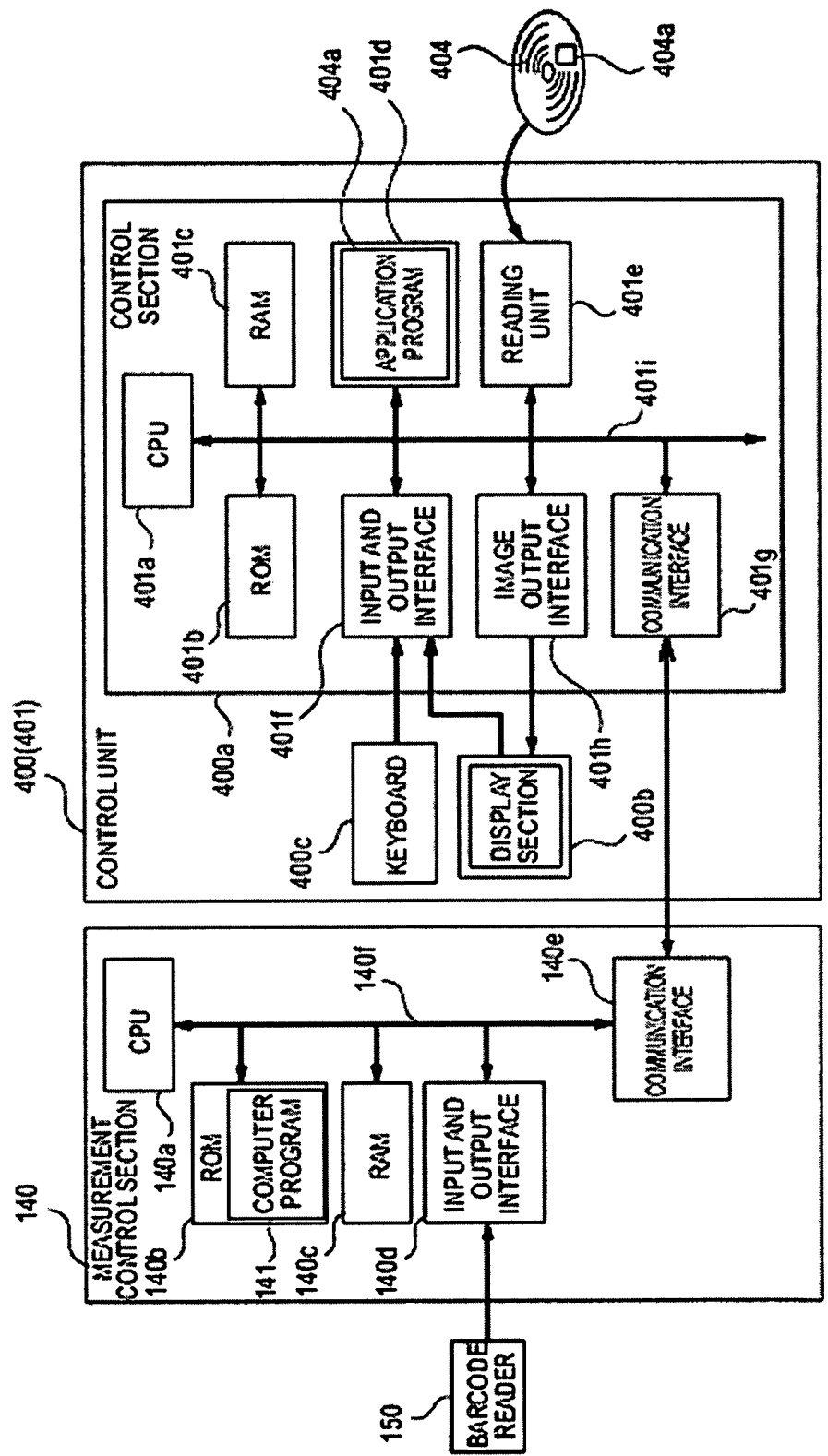
FIG. 3 is a block diagram showing a structure of a measurement control section and a control unit of the device for immunoassay shown in FIG. 1.

The measurement control section 140 mainly comprises a CPU 140a, a storing section formed from a ROM 140b, the RAM 140c and such, an input and output interface 140d and a communication interface 140e, as shown in FIG. 3. The CPU 140a, the ROM 140b, the RAM 140c, the input and output interface 140d and the communication interface 140e are connected through a bus 140f.

The CPU 140a is able to execute a computer program 141 stored in the ROM 140b and a computer program loaded into the RAM 140c.

The ROM 140b is formed from a mask ROM, a PROM, an EPROM, an EEPROM and the like. In the ROM 140b, a computer program to be executed by the CPU 140a, data used for the computer program and such are recorded.

The RAM 140c is formed from a SRAM, a DRAM or the like. The RAM 140c is used for reading a computer program recorded in the ROM 140b.

The RAM 140c is also used as an operation area of the CPU 140a in executing the computer program.

The input and output interface 140*d* is formed from a serial interface such as a USB, an IEEE 1394 and an RS-232C, a parallel interface such as a SCSI, an IDE and an IEEE 1284 or an analog interface formed from a D/A converter, an A/D converter or the like, for example. The input and output interface 140*d* is connected to a bar code reader 150. The test tube 3 (refer to FIG. 1) for containing a specimen and the rack 4 (refer to FIG. 1) for holding the plural test tubes 3 are marked with bar codes in which information for specifying the specimen in the test tube 3 or the rack 4 is recorded. The bar code reader 150 is used for reading the bar codes marked on the test tube 3 and the rack 4.

The communication interface 140*e* is an Ethernet (the registered trademark) interface, for example. The communication interface 140*e* allows the measurement control section 140 to send and receive data to and from a computer 401 through a predetermined communication protocol.

[Structure of Control Unit]

The control unit 400 is formed from a personal computer 401 (PC) or the like and includes a control section 400*a*, a display section 400*b* and an input section (an input means) 400*c* such as a keyboard and a mouse, as shown in FIG. 1. The control section 400*a* has a function of performing control of an operation of each mechanism of the measurement unit 2 and analyzing optical information of a specimen, the information being obtained in the measurement unit 2. The control section 400*a* is formed from a CPU, a ROM, a RAM or the like. The display section 400*b* is used for displaying information such as a result of analysis, which has been obtained in the control section 400*a*, and the like.

Now, described will be each structure of the control unit 400. The control section 400*a* mainly comprises a storing section, which is formed from a CPU 401*a*, a ROM 401*b*, a RAM 401*c*, a hard disc 401*d* and such, a reading unit 401*e*, an input and output interface 401*f*, a communication interface 401*g* and an image output interface 401*h*, as shown in FIG. 3.

The CPU 401*a*, the ROM 401*b*, the RAM 401*c*, the hard disc 401*d*, the reading unit 401*e*, the input and output interface 401*f*, the communication interface 401*g* and the image output interface 401*h* are connected via a bus 401*i*.

The CPU 401*a* is able to execute a computer program stored in the ROM 401*b* and a computer program loaded into the RAM 401*c*. Executing a later-mentioned application program 404*a* by the CPU 401*a* allows the computer 401 to function as the control unit 400.

The ROM 401*b* is formed from a mask ROM, a PROM, an EPROM, an EEPROM or the like. In the ROM 401*b*, recorded are a computer program to be executed by the CPU 401*a*, data used for the computer program and the like.

The RAM 401*c* is formed from a SRAM, a DRAM and such. The RAM 401*c* is used for reading a computer program recorded in the ROM 401*b* and the hard disc 401*d*. The RAM 401*c* is also used as an operation area of the CPU 401*a* in executing the computer program.

In the hard disc 401*d*, installed are various kinds of computer program 404*a*, which is to be executed by the CPU 401*a*, such as an operating system and an application program and data used for executing the computer program. An application program for registering a measurement order and an application program for carrying out a later-mentioned abnormality process of the measurement unit 2, for example, are also installed in the hard disc 401*d*.

The reading unit 401*e* is formed from a flexible disc drive, a CD-ROM drive, a DVD-ROM drive or the like and capable of reading a computer program or data, which is recorded in a portable recording medium 404. The portable recording medium 404 stores an application program 404*a* in accordance with the embodiment. The computer 401 can read the application program 404*a* from the portable recording medium 404 to install the application program 404*a* into the hard disc 401*d*.

The application program 404*a* is not only provided from the portable recording medium 404. The application program 404*a* can also be provided through an electric communication line (no matter whether the communication line is cabled or radio) from external equipment connected to the computer 401 via the electric communication line so as to be capable of communication. The application program 404*a* is stored in a hard disc of a server computer in the Internet, for example. The computer 401 accesses the server computer to download the application program 404*a*. The downloaded application program 404*a* can be installed in the hard disc 401*d*.

In the hard disc 401*d*, for example an operating system for providing a graphical user interface environment such as the Windows (the registered trademark) manufactured and sold by the Microsoft Corp. in the United States is installed. The application program 404*a* in accordance with the embodiment is assumed to operate in the operating system in the following description.

The input and output interface 401*f* is formed from a serial interface such as a USB, an IEEE 1394 and an RS-232C, a parallel interface such as a SCSI, an IDE and an IEEE 1284 or an analog interface formed from a D/A converter, an A/D converter or the like, for example. The input and output interface 401*f* is connected to a keyboard 400*c*. Using the keyboard 400*c* by a user allows data to be inputted into the computer 401.

The communication interface 401*g* is an Ethernet (the registered trademark) interface, for example. The communication interface 401*g* allows the computer 401 to send and receive data to and from a measurement unit 2 through a predetermined communication protocol.

The image output interface 401*h* is connected to the display section 400*b* formed from an LCD, a CRT or the like. The image output interface 401*h* is arranged to output to the display section 400*b* an image signal corresponding to image data given by the CPU 401*a*. The display section 400*b* displays an image (a screen) in accordance with an inputted image signal.

[Whole Process]

Figure 4:
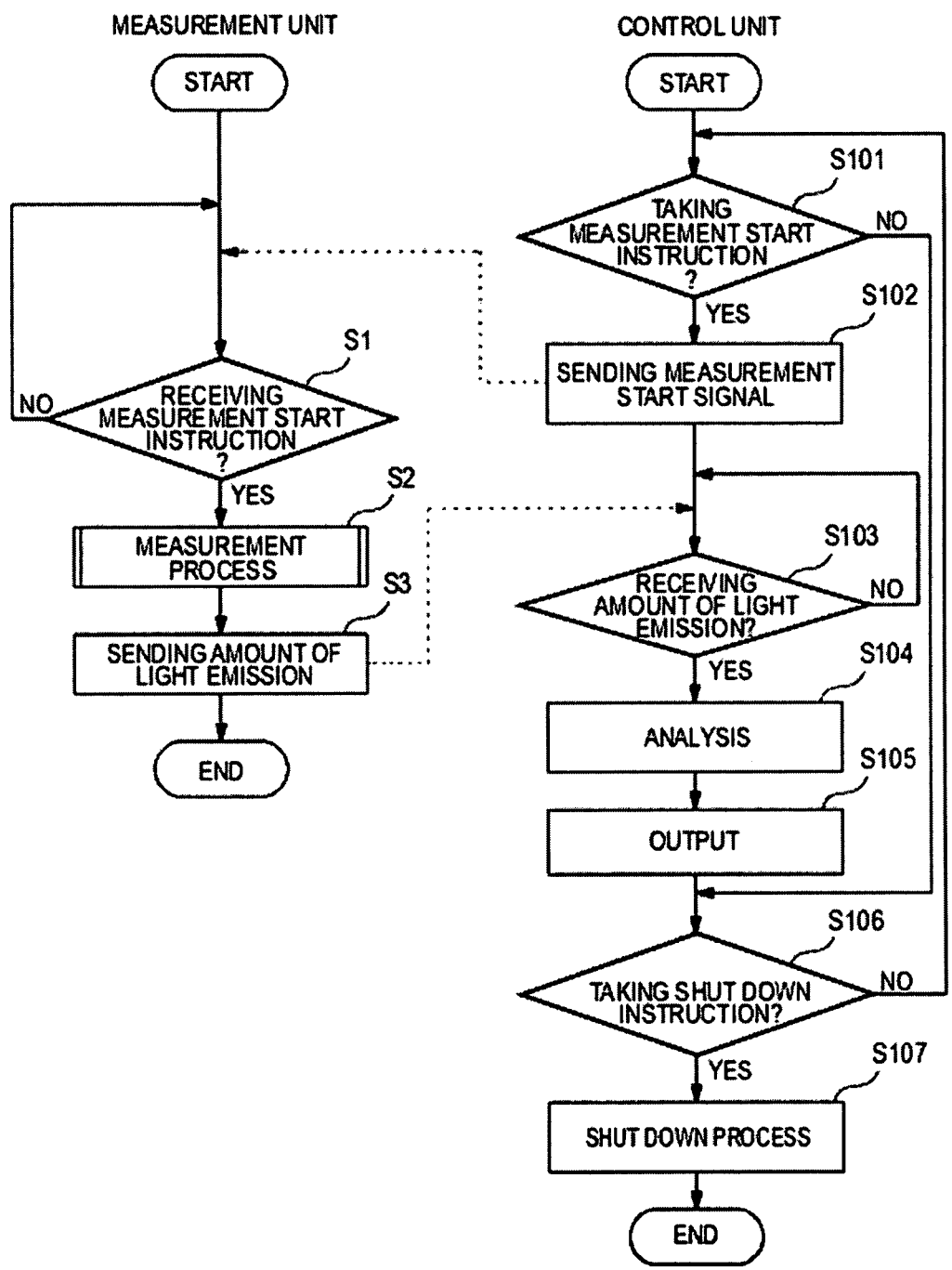
FIG. 4 is a flowchart showing a whole of an analyzing process of the device for immunoassay shown in FIG. 1.

FIG. 4 is a flowchart of a whole process of the analysis by means of the device for immunoassay 1.

First, the control section 400*a* judges whether an instruction to start measurement is given or not in Step S101. In the case that the instruction to start measurement is judged to have been given (Yes), the control section 400*a* advances the process to Step S102. The process is advanced to Step S106 in the case of judgment that the instruction to start measurement has not been given (No). The control section 400*a* then sends a measurement start signal to the measurement control section 140 in Step S102.

Following to the above, the measurement control section 140 judges whether the measurement start signal has been received or not in Step S1. A measurement process is carried out in Step S2 when the measurement control section 140 judges that the measurement start signal has been received (Yes). After the measurement is completed, the measurement control section 140 sends data of the amount of light emission to the control section 400*a* in Step S3 as a result of the measurement.

The control section 400*a* judges whether the data of the amount of light emission has been received from the measurement control section 140 or not in Step S103. A process of analyzing the data of the amount of light emission is carried out in Step S104 in the case that the data of the amount of light emission has been received (Yes). That is to say, the control section 400a calculates concentration of an antigen subject to the measurement on the basis of a sent result of the measurement and a calibration curve, which is formed in advance by means of a standard sample and stored in the hard disc 401d, and stores the result (a result of the analysis). The control section 400a then outputs the result of the analysis in Step S105.

The control section 400a judges whether an instruction to shut down the personal computer 401 has been received or not in Step S106. The control section 400a advances the process to Step S107 in the case of judgment that the instruction to shut down the personal computer 401 has been received (Yes). The process is returned to Step S101 when it is judged that the instruction to shut down the personal computer 401 has not been received (No). In Step S107, the control section 400a shuts down the personal computer 401 to complete the process.

[Measurement Process]

FIG. 5 is a flowchart of the measurement process in Step S2 in FIG. 4. A process of measurement by means of the device for immunoassay 1 will be described, made reference to FIGS. 5 and 1.

(Process of Supplying Cuvette)

First, a cuvette is carried to and set in the holding section 81a of the primary reaction table 81 of the primary reaction section 80a by means of the cuvette supplying section, which is not shown, in Step S21.

(Process of Dispensing Reagent R1)

In Step S22, the reagent dispensation section 90a sucks the reagent R1 in a reagent container set on the reagent table 60a by means of the nozzle section, and then, rotates the arm section 91b toward the primary reaction section 80a to discharge the sucked reagent R1 into the cuvette held on the holding section 81a of the primary reaction table 81. The reagent R1 includes a capture antibody to be combined with an antigen included in a specimen.

(Process of Dispensing Specimen)

Following to the above, the specimen dispensation section 50 mounts a pipette chip, which is to be carried to the carrying rack of the urgent specimen and chip carrying section 20, and then, sucks a specimen such as blood from the test tube 3 placed in the rack 4 having been carried to the sucking position by means of the specimen carrying section 10 in Step S23. The specimen dispensation section 50 then rotates the arm section 51 toward the primary reaction section 80a to discharge the sucked specimen into the cuvette in which the reagent R1 has been dispensed in the process of dispensing the reagent R1.

After the above, the container carrying section 82 of the primary reaction section 80a is used to stir the cuvette in which the reagent R1 and the specimen are contained. The stirred reagent R1 and specimen are incubated in the cuvette on the holding section 81a of the primary reaction table 81 for a predetermined period of time. This results in combination of a capture antibody (the reagent R1) with an antigen of the specimen.

(Process of Dispensing Reagent R2)

Following to the above, in Step S24, the reagent dispensation section 90b sucks the reagent R2 in a reagent container set on the reagent table 60b by means of the nozzle section, and then, rotates the arm section 92b toward the primary reaction section 80a to discharge the sucked reagent R2 into the cuvette in which the reagent R1 and the specimen have been incubated for a predetermined period of time are contained. The reagent R2 includes a magnetic particle to be combined with the capture antibody combined with the antigen included in the specimen.

After the above, the container carrying section 82 of the primary reaction section 80a is used to stir the cuvette in which the reagent R1, the specimen and the reagent R2 are contained. The stirred reagent R1, specimen and reagent R2 are incubated in the cuvette on the holding section 81a of the primary reaction table 81 for a predetermined period of time. This results in combination of the magnetic particle (the reagent R2) with the capture antibody (the reagent R1) combined with the antigen of the specimen.

(Carrying Process from Primary Reaction Section 80a to Primary B/F Separation Table 101)

Following to the above, the cuvette containing the incubated reagent R1, specimen and reagent R2 is carried to the primary B/F separation table 101 by means of the container carrying section 82 of the primary reaction section 80a in Step S25.

(Process of Eliminating Unnecessary Component by Means of Primary B/F Separation Section 100a)

The magnetic particle in the cuvette held on the primary B/F separation table 101 is magnetically collected by means of a magnet provided on a side of the cuvette in Step S26, following to the above. A nozzle section of the primary B/F separation section 100a is then inserted into the cuvette to suck a sample. This causes an unnecessary component other than the magnetic particle and the antigen combined with the magnetic particle through the capture antibody to be eliminated.

In order to eliminate the unnecessary component more certainly, repeatedly carried out is an operation of supplying the cuvette with a rinse liquid, stirring the liquid, and then, eliminating the unnecessary component together with the rinse liquid by means of the nozzle section.

The cuvette after the unnecessary component has been eliminated is transferred to a position capable of holding by means of the arm section 96a of the carrying mechanism 96 by a rotation of the primary B/F separation table 101.

(Carrying Process from Primary B/F Separation Table 101 to Secondary Reaction Part 80b)

The cuvette in which the unnecessary component is eliminated by means of the primary B/F separation section 100a is then held on the arm section 96a of the carrying mechanism 96 to be carried to the holding section 83a of the secondary reaction table 83 of the secondary reaction section 80b, as shown in FIG. 1, in Step S27.

(Process of Dispensing Reagent R3)

Following to the above, in Step S28, the reagent dispensation section 90c sucks the reagent R3 in a reagent container set on the reagent table 60a by means of the nozzle section, and then, rotates the arm section 93b toward the secondary reaction section 80b to discharge the predetermined amount of reagent R3 into the cuvette containing the magnetic particle (the reagent R2) combined via the capture antibody (the reagent R1) and the antigen of the specimen. The reagent R3 includes a labeled antibody to be combined with the antigen included in the specimen.

After the above, the container carrying section 84 of the secondary reaction section 80b is used to stir the cuvette in which the capture antibody (the reagent R1), the antigen (the specimen), the magnetic particle (the reagent R2) and the reagent R3 including the labeled antibody are contained. The capture antibody (the reagent R1), the antigen (the specimen), the magnetic particle (the reagent R2) and the reagent R3 including the labeled antibody, which have been stirred, are incubated in the cuvette on the holding section 83a of the secondary reaction table 83 for a predetermined period of time. This results in combination of the antigen, which has been combined with the magnetic particle (the reagent R2) through the capture antibody (the reagent R1), with the labeled antibody (the reagent R3).

(Carrying Process from Secondary Reaction Section 80*b* to Secondary B/F Separation Table 102)

Following to the above, the cuvette containing the capture antibody (the reagent R1), the antigen (the specimen), the magnetic particle (the reagent R2) and the reagent R3 including the labeled antibody is carried to the secondary B/F separation table 102 by means of the container carrying section 84 of the secondary reaction section 80*b* in Step S29.

(Process of Eliminating Unnecessary Component by Means of Secondary B/F Separation Section 100*b*)

Similarly to the process by means of the primary B/F separation section 100*a*, the magnetic particle in the cuvette held on the secondary B/F separation table 102 is magnetically collected by means of a magnet provided on a side of the cuvette in Step S30, following to the above. A nozzle section of the secondary B/F separation section 100*b* is then inserted into the cuvette to suck a sample. This causes an unnecessary component other than the magnetic particle and the antigen combined with the magnetic particle through the capture antibody to be eliminated. In order to eliminate the unnecessary component more certainly, repeatedly carried out is an operation of supplying the cuvette with a rinse liquid, stirring the liquid, and then, eliminating the unnecessary component together with the rinse liquid by means of the nozzle section.

The cuvette containing a sample including the antigen combined with the labeled antibody, the cuvette in which the unnecessary component has been eliminated, is transferred to a position where the container carrying section 84 of the secondary reaction section 80*b* can carry the cuvette by a rotation of the secondary B/F separation table 102.

(Carrying Process from Secondary B/F Separation Table 102 to Secondary Reaction Part 80*b*)

The cuvette in which the unnecessary component has been eliminated by means of the secondary B/F separation section 100*b* is then carried to the holding section 83*a* of the secondary reaction table 83 again by means of the container carrying section 84 of the secondary reaction section 80*b* in Step S31.

(Process of Dispensing Reagent R4)

Following to the above, in Step S32, the R4 reagent dispensation section 90*d* discharges the reagent R4 (a dispersing liquid) in a reagent container, which is provided at a lower part of the device for immunoassay 1 and which is not shown, into the cuvette containing the capture antibody (the reagent R1), the magnetic particle (the reagent R2), the labeled antibody (the reagent R3) and the antigen of the specimen through a nozzle section.

(Process of Dispensing Reagent R5)

Following to the above, in Step S33, the R5 reagent dispensation section 90*e* discharges the reagent R5 in a reagent container, which is provided at a lower part of the device for immunoassay 1 and which is not shown, into the cuvette containing the capture antibody (the reagent R1), the magnetic particle (the reagent R2), the labeled antibody (the reagent R3), the dispersing liquid (the reagent R4) and the antigen of the specimen through a nozzle section. The reagent R5 includes a luminescent substrate emitting light in reaction to the labeled antibody of the reagent R3.

The container carrying section 84 of the secondary reaction section 80*b* is then used to stir the cuvette in which the capture antibody (the reagent R1), the antigen (the specimen), the magnetic particle (the reagent R2), the labeled antibody (the reagent R3), the dispersing liquid (the reagent R4) and the reagent R5 including the luminescent substrate are contained. The capture antibody (the reagent R1), the antigen (the specimen), the magnetic particle (the reagent R2), the labeled antibody (the reagent R3), the dispersing liquid (the reagent R4) and the reagent R5 including the luminescent substrate, which have been stirred, are incubated in the cuvette on the holding section 83*a* of the secondary reaction table 83 for a predetermined period of time.

(Process of Measurement (Light Measurement))

After the above, the cuvette containing the capture antibody (the reagent R1), the antigen (the specimen), the magnetic particle (the reagent R2), the labeled antibody (the reagent R3), the dispersing liquid (the reagent R4) and the reagent R5 including the luminescent substrate, which have been incubated, is carried to a position of measurement by means of the carrying mechanism section 121 of the detection section 120 in Step S34. The amount of light emission (the amount proportional to the number of photons) generated in a reaction process between the labeled antibody of the reagent R3 and the luminescent substrate of the reagent R5 is then obtained by means of a photomultiplier (not shown).

The obtained result of the measurement is sent to the control section 400*a* in Step S3 in FIG. 4.

The cuvette containing the measured sample is carried to a position under a sucking section (not shown) by means of the carrying mechanism section 121 of the detection section 120. The measured sample is sucked by means of the sucking section to empty the cuvette. The cuvette is then carried to a position corresponding to a disposal hole 130 by means of the carrying mechanism section 121 to be discarded into a trash can, which is provided under the device for immunoassay 1 and which is not shown, through the disposal hole 130.

[Detection of Operation Error (Abnormality) in Each Mechanism Section of Measurement Unit]

Respective mechanism sections of the measurement unit 2 such as the specimen dispensation section 50, the reagent table 60, the reagent dispensation section 90, the primary and secondary reaction sections 80*a* and 80*b*, the primary and secondary B/F separation sections 100*a* and 100*b*, the primary and secondary B/F separation tables 101 and 102 and the detection section 120 are arranged so as to be driven by motors 50*m*, 60*m*, 80*am*, 80*bm*, 90*m*, 100*am*, 100*bm*, 101*m* and 102*m*, respectively, as shown in FIG. 2. The specimen dispensation section 50, the reagent dispensation section 90 and the primary and secondary B/F separation sections 100*a* and 100*b*, for example, comprise nozzle sections for sucking and discharging a specimen, a reagent and the like and are arranged to move the nozzle sections in the vertical direction or rotate (turn) by means of the motors. Further, the reagent table 60, the primary and secondary reaction tables 81 and 83 (refer to FIG. 1) and the primary and secondary B/F separation tables 101 and 102 are arranged to be rotated by means of the motors.

Moreover, conditions of operations of the respective mechanism sections are arranged to be detected by means of the sensors 50*s*, 60*s*, 80*as*, 80*bs*, 90*s*, 100*as*, 100*bs*, 101*s*, 102*s* and 120*s*. The sensors include a contact or non-contact (transmission) type origin position sensor for detecting an origin position (a position of a starting point (an ending point) of an operation) of each mechanism section, an encoder for detecting the number of pulse of a motor, a collision sensor for detecting collision of a nozzle section with an obstacle, a sensor for detecting a cuvette held on the table and such.

The measurement control section 140 of the measurement unit 2 obtains a detection result from each sensor to analyze the detection result. In the case that an error in operation is judged to exist in each mechanism section on the basis of the analysis, an error signal is sent to the control unit 400.

(Example of Error in Operation)

The reagent dispensation sections 90a to 90c, for example, suck the reagents from the reagent tables 60a and 60b, discharge the reagents in the cuvette held on the holding section 81a of the primary reaction table 81 of the primary reaction section 80a, and then, returns to their origin positions. In the case, however, that the origin position sensor detects no return to the origin position even after completing the operation, the measurement control section 140 sends an error signal indicating that abnormality occurs to the reagent dispensation sections 90a to 90c.

Further, the specimen dispensation section 50 receives an instruction from the measurement control section 140 so as to, in moving the nozzle section between the origin position and a sucking position of a specimen (a position of the test tube 3), rotate a shaft of a motor as many times as the number of driving pulse corresponding to a distance of the movement. In the case, however, that a difference between an actual pulse number of the motor, which is detected by means of an encoder, and the instructed number of driving pulse is more than a predetermined value, it can be considered that the motor has been broken down or that an arm section 51 of the specimen dispensation section 50 or the like has collided with an obstacle. Accordingly, the measurement control section 140 sends an error signal indicating that abnormality occurs in the specimen dispensation section 50 to the control unit 400 in such a case.

The control unit 400 performs control corresponding to the error signal for the respective mechanism sections of the measurement unit 2 in receiving the error signal from the measurement control section 140. Now, described in detail will be the process (an abnormality control process) hereinafter.

[Abnormality Control Process of Measurement Unit]

The control unit 400 in accordance with the embodiment is arranged to control an operation of each mechanism section on the basis of a stage where abnormality occurs, the stage being one of three stages (first to third stages) obtained by logically dividing the measurement process (refer to FIG. 5) of the measurement unit 2. The first to third stages are set so that predetermined abnormality occurring in one stage would have no influence on the other stages on the downstream side (in a subsequent process) thereof but have an influence on other operations in the same stage.

Concretely, it is assumed in the embodiment that the process from the start of the measurement to Step S28 is the first stage ST1, the process from Step S29 to Step S31 is the second stage ST2 and the process from Step S32 to the end of the measurement is the third stage ST3, as shown in FIG. 5. The respective stages will be described in detail hereinafter.

(Detail of First Stage)

The first stage ST1 is the process from the start of the measurement to an operation that the reagent dispensation section 90c is used to dispense the reagent R3 in the cuvette of the secondary reaction section 80b from the reagent table 60a (before the cuvette is carried to the subsequent secondary B/F separation table 102) (from Step S21 to Step S28).

When predetermined abnormality occurs in a certain mechanism section in the first stage ST1, other mechanism sections in the same first stage ST1 may be somewhat influenced. Description will be made on the assumption that the abnormality occurs in an operation of dispensing the reagent R1 in the cuvette of the primary reaction section 80a by means of the reagent dispensation section 90a (Step S22 in FIG. 5), for example.

In the case that the motor stops due to abnormality under the condition that a pipette of the reagent dispensation section 90a is inserted in the cuvette of the primary reaction section 80a, for example, rotating the primary reaction table 81 of the primary reaction section 80a as it is has a possibility of a damage of the arm section 91 or the pipette of the reagent dispensation section 90a. Further, proper rotation of the primary reaction table 81 is likely to be impossible, so that the other mechanism sections of the primary reaction table 81, which directly operate on the cuvette, such as the container carrying section 82 for carrying the cuvette between the container carrying section 82 and the specimen dispensation section 50 or the reagent dispensation section 90b, which dispenses the specimen or the reagent R2 in the cuvette, or the primary B/F separation table 101, for example, cannot be properly operated. Accordingly, the abnormality has an influence on the operations in Step S23 to Step S25 in FIG. 5.

Moreover, in the case that the motor stops due to abnormality under the condition that a pipette of the reagent dispensation section 90a is inserted in the reagent container of the reagent table 60a, rotating the reagent table 60a as it is has a possibility of a damage of the arm section 91 or the pipette of the reagent dispensation section 90a. Furthermore, proper rotation of the reagent table 60a is likely to be impossible, so that another mechanism section directly operating upon the reagent table 60a, the reagent dispensation section 90c for sucking the reagent R3, for example, cannot be properly operated. Accordingly, the abnormality also has an influence on an operation in Step S28.

(Detail of Second Stage)

On the other hand, the second stage ST2 is a process of carrying the cuvette from the secondary reaction table 83 to the secondary B/F separation table 102, performing a secondary B/F separation process by means of the secondary B/F separation section 100b, and then, carrying the cuvette again to the secondary reaction table 83 (before dispensing the reagent R4 by means of the reagent dispensation section 90d) (Steps S29 to S31 in FIG. 5). Accordingly, it is possible to perform an operation without receiving any influence from the abnormality in the first stage ST1.

In the case of occurrence of predetermined abnormality in the second stage ST2, other operations in the same second stage receive influence in some cases. In the case that the container carrying section 84 fails to catch the cuvette on the secondary separation table 102 during the operation of carrying the cuvette from the secondary B/F separation table 102 to the secondary reaction table 83 (in Step S31 in FIG. 5), for example, the subsequent secondary B/F separation process cannot be carried out. The abnormality thus has an influence on the operations in Steps S29 and S30.

(Detail of Third Stage)

On the other hand, the third stage ST3 is a process from an operation of dispensing the reagent R4 in the cuvette on the secondary reaction table 83 by means of the reagent dispensation section 90d to the end of the measurement (the end of the operation by the detection section 120) (Steps S32 to S34 in FIG. 5), the process starting after the cuvette having undergone the secondary B/F separation returns to the secondary reaction table 83. Accordingly, the process has no influence from the abnormality having occurred in the second stage ST2.

In the case of occurrence of predetermined abnormality in a certain mechanism section in the third stage ST3, other mechanism sections in the same third stage ST3 receive influence in some cases. An operation of the reagent dispensation section 90e for the reagent R5, which directly operates on the cuvette on the secondary reaction table 83, or an operation of the carrying mechanism 121 of the detection section 120, which carries the cuvette from the secondary reaction table 83, cannot be properly performed in some cases when abnormality occurs during the operation of dispensing the reagent R4 in the cuvette on the secondary reaction table 83 by means of the reagent dispensation section 90d (in Step S32 in FIG. 5), for example. The abnormality thus has an influence on Steps S33 and S34.

(Abnormality Control Process by Control Unit)

The control unit 400 controls the measurement unit 2 so that the process of the first stage would be stopped while the processes of the second and third stages ST2 and ST3 would be continued when predetermined abnormality occurs in a certain mechanism section in the first stage ST1.

Further, in the case that predetermined abnormality occurs in a certain mechanism section in the second stage ST2, the measurement unit 2 is controlled so that the process in the first and second stages would be stopped while the process in the third stage ST3 would be continued.

Moreover, the control unit 400 controls the measurement unit 2 so that all of the processes in the first to third stages would be stopped in the case of occurrence of predetermined abnormality in a certain mechanism section in the third stage ST3.

Such a flow of the abnormality control of the measurement unit 2 will be described with reference to FIG. 6. FIG. 6 is a flowchart of the process of abnormality control carried by the control unit 400 having received an error signal from the measurement control section 140.

First, the control section 400a of the control unit 400 judges in Step S121 whether or not the abnormality recognized in accordance with the error signal is predetermined abnormality having occurred in any of the reagent dispensation sections 90a to 90c for the reagent R1 to R3, the specimen dispensation section 50 and the primary B/F separation section 100a, that is, whether or not the abnormality is predetermined abnormality having occurred in the first stage ST1. The process goes to Step S122 when it is judged that the abnormality is the predetermined abnormality having occurred in any of the reagent dispensation sections 90a to 90c for the reagent R1 to R3, the specimen dispensation section 50 and the primary B/F separation section 100a. The process goes to Step S123 when the abnormality is judged not to be the predetermined abnormality having occurred in any of the reagent dispensation sections 90a to 90c for the reagent R1 to R3, the specimen dispensation section 50 and the primary B/F separation section 100a.

In Step S122, the control section 400a controls the reagent dispensation sections 90a to 90c for the reagents R1 to R3, the specimen dispensation section 50, the primary B/F separation section 100a, the primary B/F separation table 101 and the primary reaction section 80a (the primary reaction table 81) to stop the dispensation operations of the reagent dispensation sections 90a to 90c for the reagents R1 to R3, the dispensation operation of the specimen dispensation section 50, the separation operation of the primary B/F separation section 100a, the transfer operation of the primary B/F separation table 101 and the transfer operation of the primary reaction section 80a. Further, the secondary B/F separation section 100b, the secondary B/F separation table 102, the R4 and R5 reagent dispensation sections 90d and 90e, the secondary reaction section 80b and the detection section 120, which are other than the former mechanism sections, are controlled so that their operations would be continued. That is to say, the process in the first stage ST1 is stopped while the processes in the second and third stages ST2 and ST3 are continued as they are. This means that the specimen where the reagents R1 to R3 have been dispensed in the first stage undergoes measurement through the second and third stages ST2 and ST3. This allows waste of a reagent or a specimen to be suppressed.

Further, stop of the operations of the reagent dispensation sections 90a to 90c for the reagents R1 to R3, the specimen dispensation section 50, the primary B/F separation section 100a, the primary B/F separation table 101 and the primary reaction section 80a (the primary reaction table 81) allows a damage of a component or the like due to continuance of the operations to be prevented.

It may be possible to completely stop the operations of the reagent dispensation sections 90a to 90c, the specimen dispensation section 50, the primary B/F separation section 100a, the primary B/F separation table 101 and the primary reaction section 80a (the primary reaction table 81) or to stop only the operation having probability of a damage of a component such as the dispensation operation and the transfer operation.

The control section 400a then judges in Step S123 whether the abnormality is predetermined abnormality having occurred in an operation related to the secondary B/F separation section 100b or not, namely, whether the abnormality is predetermined abnormality having occurred in the second stage ST2 or not. The process goes to Step S124 in the case that the abnormality is judged to be the predetermined abnormality having occurred in the container carrying section 84 or the secondary B/F separation section. The process goes to Step S125 when it is judges that the abnormality is not the predetermined abnormality having occurred in the container carrying section 84 or the secondary B/F separation section.

In Step S124, the control section 400a controls the reagent dispensation sections 90a to 90c for the reagents R1 to R3, the specimen dispensation section 50, the primary and secondary B/F separation sections 100a and 100b, the primary and secondary B/F separation tables 101 and 102 and the primary reaction section 80a (the primary reaction table 81) to stop the dispensation operations of the reagent dispensation sections 90a to 90c for the reagents R1 to R3, the dispensation operation of the specimen dispensation section 50, the separation operations of the primary and secondary B/F separation sections 100a and 100b, the transfer operations of the primary and secondary B/F separation tables 101 and 102 and the transfer operation of the primary reaction section 80a. Further, the R4 and R5 reagent dispensation sections 90d and 90e, the secondary reaction section 80b (the secondary reaction table 83) and the detection section 120, which are other than the former mechanism sections, are controlled so that their operations would be continued. That is to say, the processes in the first and second stages ST1 and ST2 are stopped while the process in the third stages ST3 is continued as it is. Accordingly, the specimen, where the reagents R1 to R3 have been dispensed in the first stage ST1 and which has completely undergone the secondary B/F separation process in the second stage ST2, undergoes measurement through the third stage ST3. This allows waste of a reagent or a specimen to be suppressed.

In Step S125, the control section 400a judges whether the abnormality is predetermined abnormality having occurred in the reagent dispensation sections 90d and 90e for the reagents R4 and R5 or the detection section 120 or not, namely, whether the abnormality is predetermined abnormality having occurred in the third stage ST3 or not. The process goes to Step S126 in the case that the abnormality is judged to be the predetermined abnormality having occurred in the reagent dispensation sections 90d and 90e for the reagents R4 and R5 or the detection section 120. The process goes to Step S127 when it is judges that the abnormality is not the predetermined abnormality having occurred in the reagent dispensation sections 90d and 90e for the reagents R4 and R5 or the detection section 120.

In Step S126, the control section 400a controls the reagent dispensation sections 90a to 90e for the reagents R1 to R5, the specimen dispensation section 50, the primary and secondary B/F separation sections 100a and 100b, the primary and secondary B/F separation tables 101 and 102, the primary and secondary reaction sections 80a and 80b (the primary and secondary reaction tables 81 and 83) and the detection section 120 to stop the dispensation operations of the reagent dispensation sections 90a to 90e for the reagents R1 to R5, the dispensation operation of the specimen dispensation section 50, the separation operations of the primary and secondary B/F separation sections 100a and 100b, the transfer operations of the primary and secondary B/F separation tables 101 and 102, the transfer operations of the primary and secondary reaction sections 80a and 80b and the detection operation of the detection section 120. That is to say, all of the processes in the first to third stages ST1 to ST3 are stopped.

In Step S127, the control section 400a judges that the abnormality is not related to the operations of the respective mechanism sections but due to another cause, and performs a process in accordance with the cause (another process). Such abnormality is applied to a case that a lack of a certain reagent during the measurement operation causes failure of the dispensation of the reagent, for example. In such a case, the control section 400a controls the measurement unit 2 so that the operation of each mechanism section of the measurement unit 2 would be continued and only a measurement item using the reagent would be skipped.

[Corresponding Relation Between Embodiment and the Invention]

In the invention (Claim 1), the first holding section for holding a container for containing a specimen, a reagent and the like to transfer the container to a predetermined position corresponds to the primary reaction table 81 for holding and transferring a cuvette (a container) in the embodiment, for example. In this case, the first mechanism section corresponds to the reagent dispensation sections 90a and 90b, the specimen dispensation section 50, the container carrying section 82 and such in the embodiment, for example. They are the mechanism sections operating in the process in the first stage ST1.

Further, in the invention, the second mechanism section corresponds to the secondary B/F separation section 100b and such in the case that the first holding section is assumed to be the primary reaction table 81 in the embodiment, for example. This is the mechanism section operating in the process in the second stage ST2.

Moreover, the abnormality control means in the invention corresponds to the control unit 400 for controlling the measurement unit 2 so that an operation of each mechanism section operating in the stage ST1 would be stopped while an operation of a mechanism section operating in the second stage ST2 would be continued in the case of occurrence of abnormality in the first stage ST1, in the embodiment.

In the invention (Claim 4), the third mechanism section corresponds to the reagent dispensation sections 90d and 90e for the reagents R4 and R5, the detection section 120 and the like in the case of assuming that the second mechanism section is the secondary B/F separation section 100b, for example, in the embodiment.

The correspondence relation between the invention and the embodiment is only an example and does not limit the invention.

The above-mentioned embodiment does not limit the invention. The invention may be properly modified in design. The invention is not limited to the device for immunoassay, for example, and may be also applied to another analyzing device such as a blood coagulation measurement device, a multi-item corpuscle analyzer, an analytical device for material component in urine and a gene amplification measurement device.

Furthermore, a cuvette (a container) is transferred from the primary reaction table 81 to the secondary B/F separation table 102 by means of plural mechanism sections but may be transferred by means of a single mechanism section.

What is claimed is:

1. A specimen analyzer including abnormality control detection, comprising:
   a first holding section for holding a container for containing at least one of a specimen, a reagent and a mixture thereof and transferring the container to a predetermined position;
   a first reagent dispensation section for executing a predetermined first dispensation operation for dispensing a reagent including a capture antibody to the container held on the first holding section;
   a secondary B/F separation table for holding the container;
   a first transfer mechanism section for transferring the container from the first holding section to the secondary B/F separation table;
   a secondary B/F separation section for a B/F separation process for a liquid contained in the container held at the secondary B/F separation table;
   a detection section configured to measure a sample for which the B/F separation process has been executed;
   an error detector configured to detect occurrence of abnormality in the first reagent dispensation section; and
   a controller configured to control operations of the first holding section, the first reagent dispensation section, and the secondary B/F separation section so that the first dispensation operation of the first reagent dispensation section and the transfer operation of the first holding section would be stopped while the B/F separation process of the secondary B/F separation section would be continued in the case that the error detector detects occurrence of abnormality in the first reagent dispensation section.

2. The specimen analyzer according to claim 1, wherein
   the error detector is further configured to detect occurrence of abnormality in the secondary B/F separation section, and
   the controller is further configured to control operations of the first holding section, the first reagent dispensation section and the secondary B/F separation section so that the transfer operation of the first holding section, the first dispensation operation of the first reagent dispensation section and the B/F separation process of the secondary B/F separation section would be stopped in the case that the error detector detects occurrence of abnormality in the secondary B/F separation section.

3. The specimen analyzer according to claim 1, further comprising
   a second reagent dispensation section for executing a predetermined second dispensation operation for dispensing at least one of a dispersing liquid and a reagent including a luminescent substrate to the container held on a second holding section,
   wherein
   the controller controls operations of the first holding section, the first reagent dispensation section, the secondary B/F separation section, and the second reagent dispensation section so that the transfer operation of the first holding section and the first dispensation operation of the first reagent dispensation section would be stopped while the B/F separation process of the secondary B/F separation section and the second dispensation operation of the second reagent dispensation section would be continued in the case that the error detector detects occurrence of abnormality in the first reagent dispensation section.

4. The specimen analyzer according to claim 3, wherein the error detector is further configured to detect occurrence of abnormality in the secondary B/F separation section, and the controller is further configured to operations of the first holding section, the first reagent dispensation section, the secondary B/F separation section, and the second reagent dispensation section so that the transfer operation of the first holding section, the first dispensation operation of the first reagent dispensation section, and the B/F separation process of the secondary B/F separation section would be stopped while the second dispensation operation of the second reagent dispensation section would be continued in the case that the error detector detects occurrence of abnormality in the secondary B/F separation section.

5. The specimen analyzer according to claim 3, wherein the error detector is further configured to detect occurrence of abnormality in the second reagent dispensation section, and the controller controls operations of the first holding section, the first reagent dispensation section, the secondary B/F separation section, and the second reagent dispensation section so that the transfer operation of the first holding section, the first dispensation operation of the first reagent dispensation section, the B/F separation process of the secondary B/F separation section, and the second dispensation operation of the second reagent dispensation section would be stopped in the case that the error detector detects occurrence of abnormality in the second reagent dispensation section.

* * * * *